United States Patent [19]

ten Broeke et al.

[11] 4,070,359
[45] Jan. 24, 1978

[54] PROCESS FOR PREPARING 5,11-DIAZATETRACYCLODODECANES

[75] Inventors: Jan ten Broeke, Somerset; Edward J. J. Grabowski, Westfield, both of N.J.; Lars M. Flataker, Lansdale, Pa.; Michael H. Fisher, Bridgewater; Arthur A. Patchett, Cranford, both of N.J.

[73] Assignee: Merck & Co., Inc., Rahway, N.J.

[21] Appl. No.: 780,731

[22] Filed: Mar. 24, 1977

Related U.S. Application Data

[62] Division of Ser. No. 676,769, April 14, 1976, Pat. No. 4,033,968.

[51] Int. Cl.$^2$ ............................................. C07D 487/08
[52] U.S. Cl. ............................. 260/293.55; 260/297 R
[58] Field of Search ..................................... 260/293.55

[56] References Cited

PUBLICATIONS

Liberatore, F. et al., *Tett. Lett.* No. 26, 2381–2384 (1971).
Hirao et al., J. Chem. Soc. Chem. Comm., 691–692 (1974).

*Primary Examiner*—Henry R. Jiles
*Assistant Examiner*—Richard A. Schwartz
*Attorney, Agent, or Firm*—William H. Nicholson; Mario A. Monaco

[57] ABSTRACT

A new heterocycle, 5,11-diazatetracyclo]6.2.2.0$^{2,7}$.0$^{4,9}$]-dodecane, is prepared by heating an endo-diazatricyclo[6.2.2.0$^{2,7}$]dodec-11-ene substituted in the 7 and 11 positions with electron withdrawing groups. 2,9-Bisphenylacetyl derivatives of the new heterocycle and closely related derivatives are potent analgesic agents.

3 Claims, No Drawings

PROCESS FOR PREPARING 5,11-DIAZATETRACYCLODODECANES

This is a division of application Ser. No. 676,769, filed Apr. 14, 1976, now U.S. Pat. No. 4,033,968.

This invention is concerned with novel 5,11-diazatetracyclo[6.2.2.0$^{2,7}$.0$^{4,9}$]dodecanes having pharmacological activity; processes for their preparation including novel intermediate compounds, a method of treating pain with the novel products; and pharmaceutical formulations employing the novel products as an active ingredient.

The novel 5,11-diazatetracyclo[6.2.2.0$^{2,7}$.0$^{4,9}$]-dodecanes of this invention having analgesic activity have structural formula:

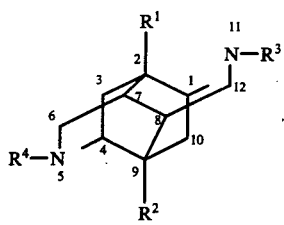

or pharmaceutically acceptable salts thereof, wherein: at least one of R$^1$ and R$^2$ is

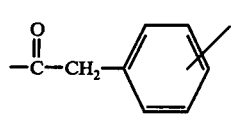

wherein R is hydrogen, halo such as fluoro, chloro, or bromo, lower alkoxy, especially C$_{1-3}$ alkoxy, or hydroxy and the other one of R$^1$ and R$^2$ is

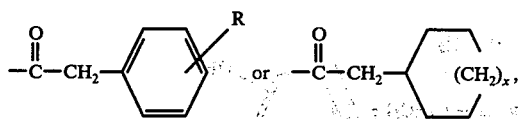

wherein x is 0 or 1; and R$^3$ and R$^4$ are the same or different and each is 1. hydrogen or
2. C$_{1-2}$ alkyl, with the proviso that they are not both hydrogen.

A preferred embodiment of the novel analgesic compounds of this invention is that wherein R$^1$ and R$^2$ each represents

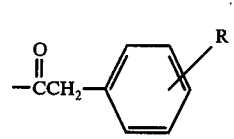

and R$^3$ and R$^4$ are as previously defined.

An even more preferred embodiment of the novel analgesic compounds is that wherein R$^1$ and R$^2$ each represents

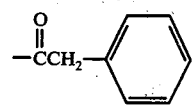

and R$^3$ and R$^4$ each represents —CH$_3$.

The novel analgesic compounds of this invention are asymmetric and exist as levo (—), and dextro (+) optical isomers or as mixtures thereof, such as racemic mixtures. All of the analgesic activity resides in those enantiomers of these novel compounds which have the same absolute configuration as the levorotatory enantiomer of 2,9-bis-phenylacetyl-5,11-dimethyl-5,11-diazatetracyclo-[6.2.2.0$^{2,7}$.0$^{4,9}$]dodecane and, therefore, these enantiomers represent an especially preferred embodiment of the novel analgesic compounds of this invention.

The pharmaceutically acceptable salts of the novel analgesic compounds of this invention are acid addition salts prepared from inorganic or organic acids and include such as bitartrate, hydrobromide, camphorsulfonate (camsylate), citrate, ethane-1,2-disulfonate(edisylate), fumarate, hippurate, hydrochloride, maleate, mandelate, methanesulfonate (mesylate), methosulfate, 2-naphthalenesulfonate (napsylate), niacinate, oxalate, 4,4'-methylenebis(3-hydroxy-2-naphthoate) (pamoate), tartrate, carbamate, succinate, acetate, ethanesulfonate (esylate), lactate, palmitate, p-toluenesulfonate (tosylate), n-acetylglycinate, benzene sulfonate, hexanoate, p-chlorobenzenesulfonate, 3-cyclopentylpropionate, heptanoate, dodecylsulfate (estolate), o-(4-hydroxybenzoyl)benzoate, 2-hydroxyethanesulfonate (isethionate), 3-phenylpropionate, trimethylacetate (pivalate, t-butylacetate, or cyclamate.

The novel analgesic compounds of this invention are prepared by a variety of processes involving a number of novel intermediates. These processes and intermediates are further embodiments of this invention and are schematically represented on the following pages.

For the sake of convenience, the novel tetracyclic analgesic and intermediate compounds having the systematic name of 5,11-diazatetracyclo[6.2.2.0$^{2,7}$.0$^{4,9}$]dodecanes are given the trivial name, diazaditwistane, following the lead of Hirao et al., J. Chem. Soc. Chem. Comm., 691 (1974) who coined the term "ditwistane" for the all carbon isostere.

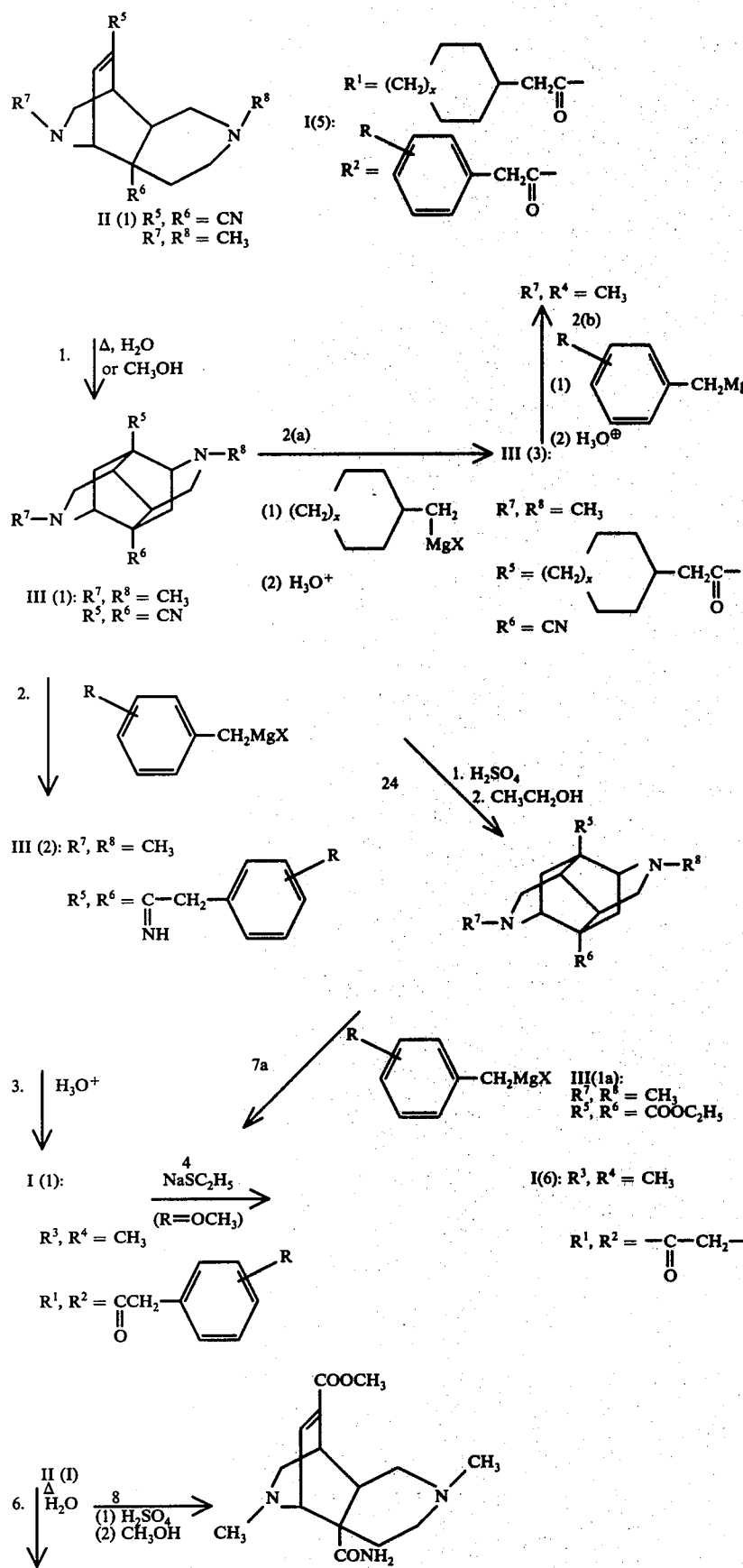

-continued
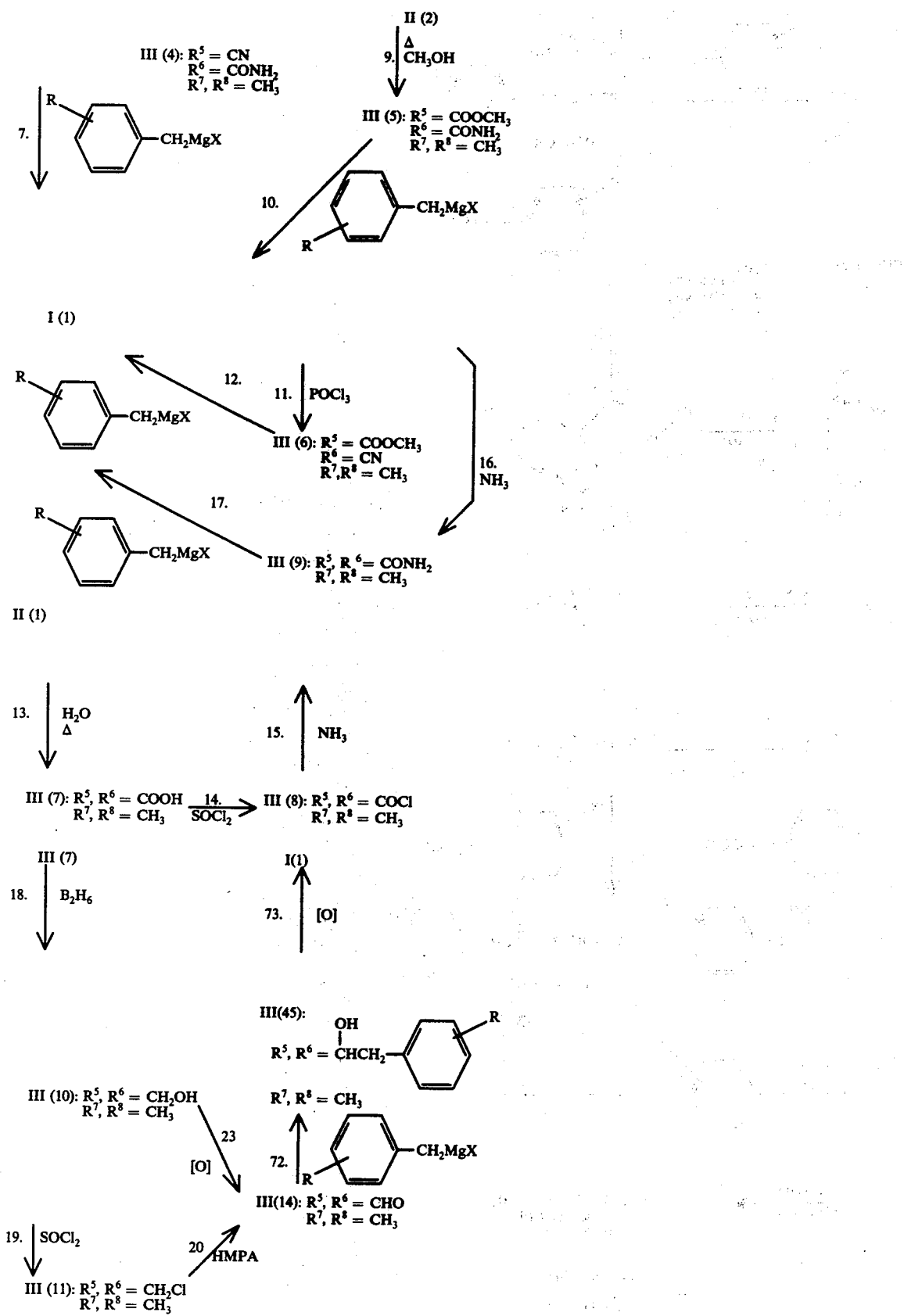

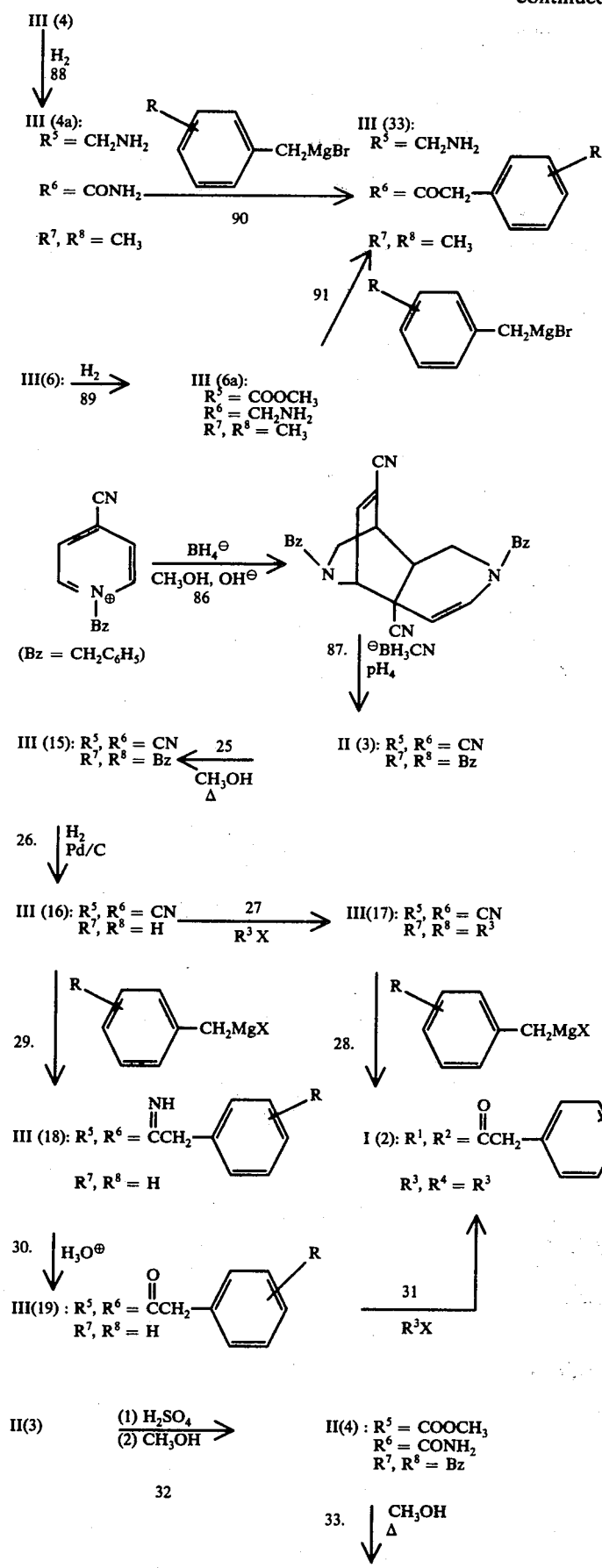

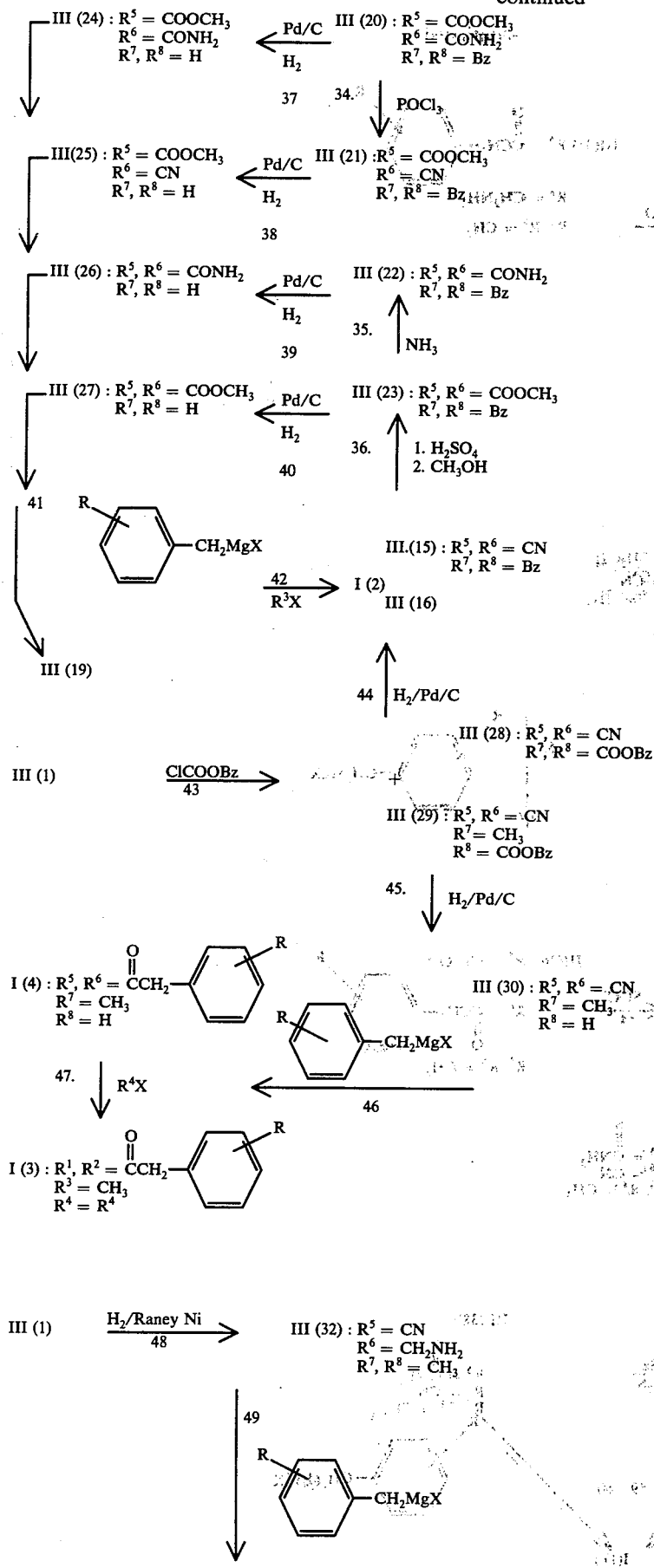

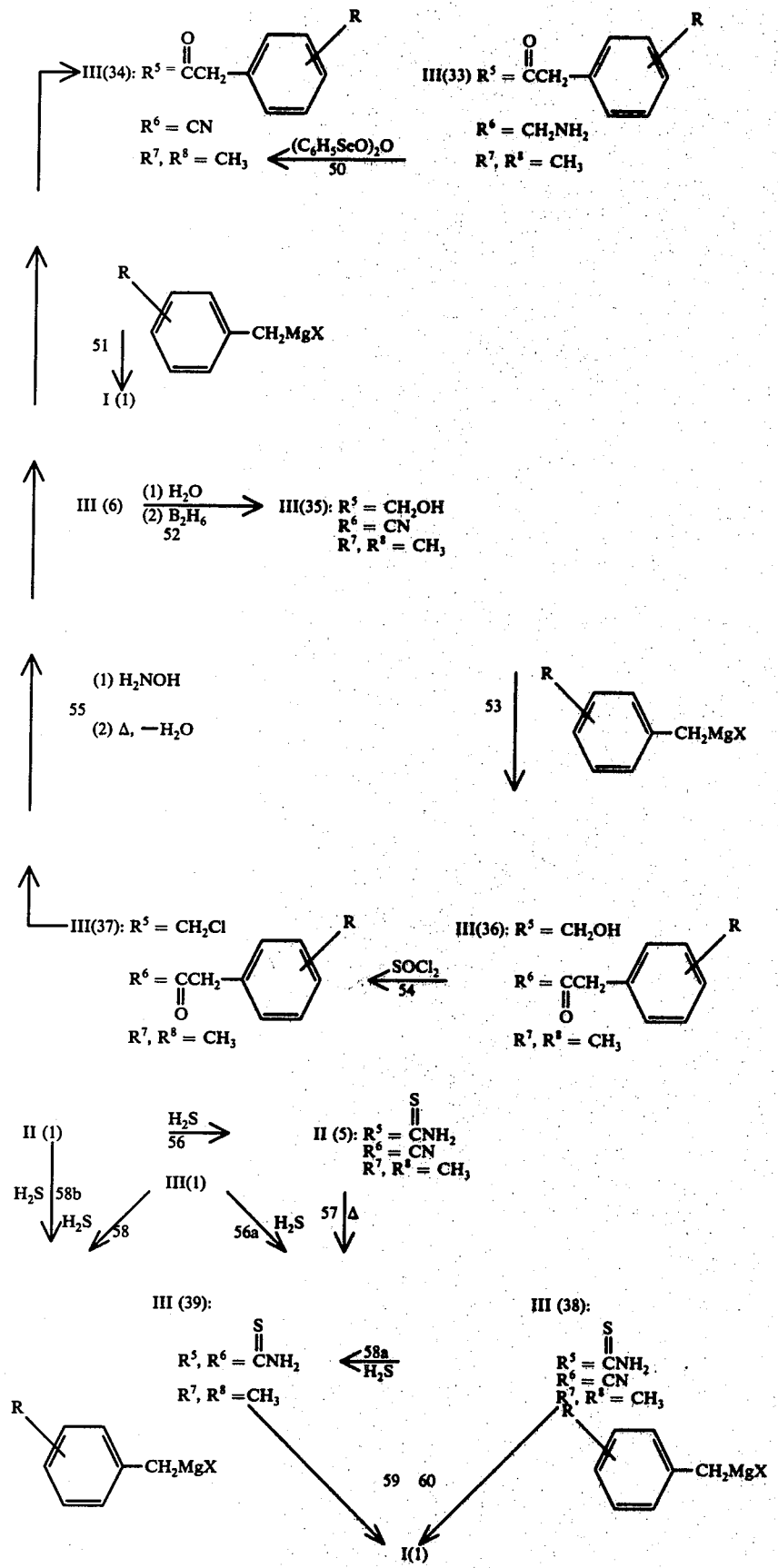

-continued
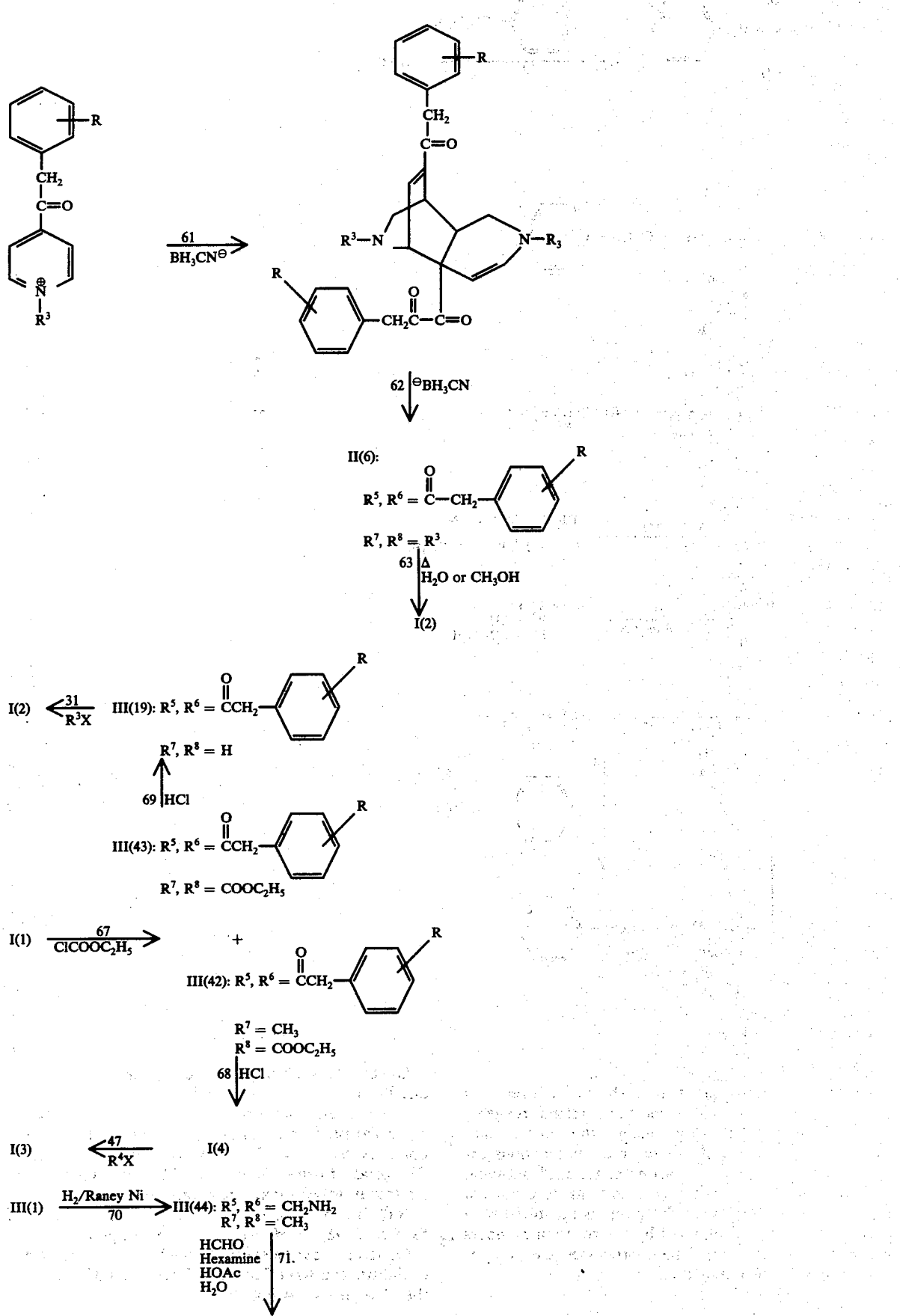

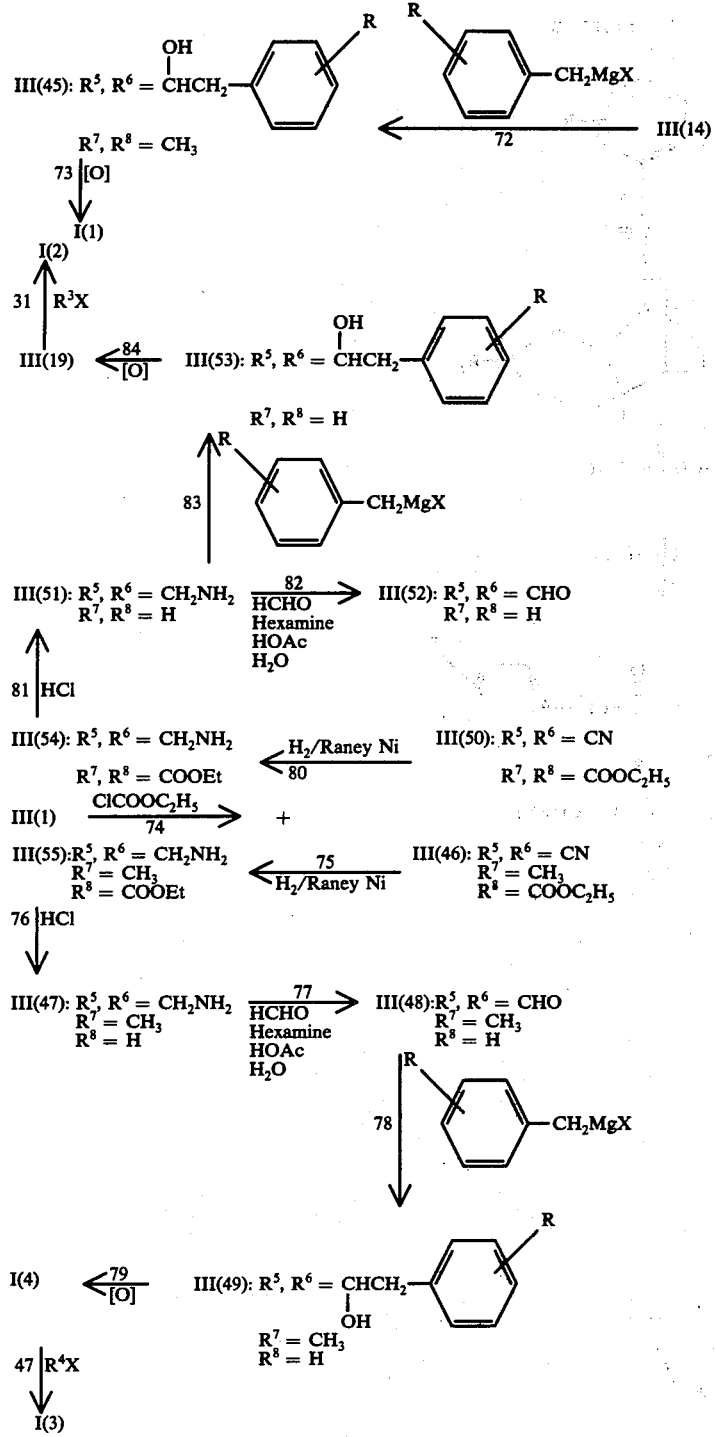

In the foregoing chemical flow sheets, each reaction has been assigned a number and the principal reagents are listed. Many of the reactions are the same or substantially the same as one or more other reactions except for the identity of the starting materials. Following are descriptions of the reaction conditions for groups of reactions. In each instance the group is identified by a letter, A, B, C, etc., followed by the reaction numbers included in that group. These processes are another embodiment of this invention.

A (1, 9, 25, 33, 57, 63)

General Procedure Tricyclic Precursors to Tetracyclic Products

The tricyclic intermediate is heated at 100°– 200° C. in a polar protic solvent such as water, methanol, ethanol, ethylene glycol, 2-methoxyethanol for 2–24 hours. The product can be isolated by filtration, aqueous precipitation, solvent concentration, or the like.

B (2, 2a, 2b, 7, 7a, 10, 12, 17, 28, 29, 41, 46, 49, 51, 53, 59, 60, 72, 78, 83, 90, 91) and 3 where applicable:

General Organometallic Procedure for Introduction of Substituted Aryl Groups — Formation of Imines and then Ketones or Alcohols The appropriately substituted tetracyclic intermediate is treated with a substituted benzyl organometallic reagent derived from such metals as magnesium, lithium, cadmium, or the like in inert solvents such as alkyl ethers, 1,2-dimethoxyethane, tetrahydrofuran, dioxane, or alkanes at temperatures from −40° C. to reflux for 1-24 hr.

For those substrates having a nitrogen at the reacting group (i.e. CN, CONH$_2$,CSNH$_2$), the reactions are quenched into aqueous solutions and the resultant imines can be isolated by filtration or extraction with common organic solvents such as chloroform, methylene dichloride, etc. Hydrolysis of the imines in aqueous acidic solution (hydrochloric, sulfuric, perchloric, hydrobromic acid, etc.) at 25°-100° C. for 1-6 hours affords the analgesic ketones.

For those substrates having no nitrogen at the reacting group, quenching into water affords the analgesics directly (from —COOR) or their carbinol precursors (from —CHO) which are oxidized in a subsequent step.

C (4)

Conversion of Aryl Ethers to Phenols

A solution of the aryl ether in dimethyl formamide is treated at reflux for 1-10 hr. with an excess of sodium thioethoxide. After addition of HCl and concentration to dryness, the crude material is recrystallized from common organic solvents to afford pure phenol.

E (6)

Conversion of tricyclic intermediate II (1) into tetracycle III (1) in water at 100° C. for 1-5 hr. affords amidonitrile III (4) as a by-product which can be isolated from the mother liquors after removal of most of III (1) by filtration.

F (8, 24, 32, 36)

General Procedure for Converting Tricyclic Dinitriles into Tricyclicamido esters or Tetracyclicdinitriles into Diesters The multicycle is treated with 2-10 volumes of concentrated sulfuric acid at 65°-125° C. for 1-10 hr. followed by quenching into 5-100 volumes of the appropriate alcohol, and heating the resulting solution at 25°-125° for 1-48 hr. thereby affording the corresponding tricyclicamido ester or tetracyclic diester.

G (11, 34)

General Amide Dehydration

Amide dehydration is achieved by reaction with reagents such as phosphorus trichloride, phosphorus oxychloride, phosphorus pentachloride, thionyl chloride, or phosgene, neat or in chlorinated solvents such as chloroform, 1,2-dichloroethane or chlorobenzene, at temperatures between 50°-150° C. for 2-10 hr. Isolation can be effected by vacuum concentration, water quenching and alkalinification to afford the corresponding nitrile.

H (13)

Combined Cyclization — Hydrolysis

Tricycle II (1) can be converted to bis-acid III (7) by cyclization and hydrolysis in water at 175°-225° C. for 2-10 hr. Concentration of the reaction solution affords bis acid III (7).

I (14)

Preparation of the Acid Chloride

Treatment of III (7) with 2-10 equivalents of thionyl chloride at reflux, followed by concentration and drying, affords acid chloride III (8) as its HCl salt.

J (15, 16, 35)

Amide Formation

Treatment of the appropriate acid chloride or ester with liquid ammonia neat or in a polar solvent such as methanol, ethanol, dimethyl formamide, dimethyl sulfoxide, hexamethylphosphoramide, or t-butanol at −40° to 100° C. for 2-10 hr. affords the corresponding amide.

K (18)

Acid III (7) is reduced by treatment with 5-8 moles of boron hydride or lithium aluminum hydride in an ether solvent such as tetrahydrofuran, dioxane, or 1,2-dimethoxyethane at 25° C.-reflux for 5-30 hr. followed by an acidic workup to destroy amine complexes. Amino alcohol III (10) is subsequently isolated by alkalinification and extraction.

L (19, 54)

Conversion of Alcohol to Chloro Compound

The alcohols are converted into their corresponding chloro compounds by treatment with reagents such as thionyl chloride, phosphorus trichloride, phosphosphorus oxychloride, phosphorus pentachloride or dichlorotriphenyl phosphorane neat or in an inert solvent such as methylene chloride, chloroform, carbon tetrachloride, 1,2-dichloroethane, or chlorobenzene at temperatures of 20° to 125° C. for 2-24 hr. Quenching into water destroys excess reagent and removes by-products, and alkalinification and extraction into common organic solvents affords the appropriate chloro compound.

M (20)

Compound III (11) is heated in 1-10 volumes of hexamethylphosphoramide at 150°-200° for 2-10 hr. to afford the corresponding aldehyde [III (14)]. The reaction is worked up by quenching into water, extraction with CH$_2$Cl$_2$ or CHCl$_3$, backwashing with water, concentration and recrystallization.

P (23)

Oxidation of alcohol III (10) can be effected by treatment with a variety of oxidizing agents under standard conditions. Treatment with activated manganese dioxide in benzene for 5-25 hr. with concurrent water removal affords aldehyde III (14). Alternately, the oxidation may be accomplished by treatment of III (10) with 6-18 eq. of CrO$_3$.2C$_5$H$_5$N in methylene chloride at 10°-40° C. for 1-5 hours to afford III (14).

R [86, 87); (61, 62)]

General Procedure for Preparation of New Tricyclic Substrates

The appropriate N-substituted (lower alkyl, lower alkenyl, benzyl or substituted benzyl)-4-cyano or 4-acylpyridinium halides are reduced and dimerized by treatment of their alcohol (methanol, ethanol) solutions at −40° to 10° C. in the presence of an alkali metal hydroxide with sodium borohydride or sodium cyanoborohydride for 1-6 hr. thereby affording dimers via Diels-Alder reactions. These are subsequently reduced by treatment with sodium borohydride or sodium cyanoborohydride in an aqueous alcoholic solvent at pH 3-7 at 0°-30° C. for 1-6 hr. to afford tricyclic adducts of type II (3) and II (5).

S (26, 37, 38, 39, 40, 44, 45)

General Debenzylation Procedure

The N-benzyl and benzyloxycarbonyl tetracyclic compounds are converted to the secondary amines by reduction with hydrogen gas at 25-200 p.s.i. over palladium on carbon or platinum oxide in an alcoholic solvent (methanol, ethanol, isopropanol) at 25°-100° C. for 1-10 hr.

T (27, 31, 42, 47)

General Alkylation Procedure 5,11-Desalkyl compounds are alkylated by treatment with the appropriate alkylating agent RX (X = Cl, Br, I,

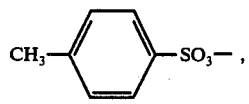

CH$_3$SO$_3$—) in an aprotic solvent such as dimethyl formamide, dimethyl sulfoxide, hexamethyl phosphoramide acetonitrile, tetrahydrofuran at 25°–100° C. for 1–24 hr. using a base such as sodium bicarbonate, sodium carbonate, potassium carbonate, calcium carbonate, or a tertiary alkyl amine to trap the formed acid.

V (43, 67, 74)

General Dealkylation Procedure 5,11-Dialkyl tetracyclic compounds can be dealkylated by reaction with 1.5–5 moles of a chloroformate (alkyl, trichloroethyl, benzyl or p-nitrobenzyl) neat or in an aprotic solvent such as benzene, chlorobenzene, toluene, xylene, or 1,2-dichloroethane at 50°–150° C. for 10–30 hr. The procedure affords a mixture of 5-alkoxycarbonyl and 5,11-bis-alkoxycarbonyl compounds which can be readily separated since the mono is a basic compound and the bis is a neutral compound. Generally, the milder conditions (i.e. 1–2 moles of reagent in benzene) favor monodealkylation whereas the more severe conditions (i.e. 5 moles neat at reflux) favor bis-dealkylation.

W (48, 70, 75, 80, 88, 89)

General Reduction of Nitriles to Aminomethyl Compounds

Dinitriles can be reduced to aminomethyl nitriles or bis-aminomethyl compounds by treatment with hydrogen gas at 1.75–140 atmospheres over Raney nickel catalyst in an alcoholic solvent such as methanol, ethanol, or isopropanol at 25°–200° C. for 20–50 hr. If the reaction is run at the milder conditions (i.e. 2.8 atmospheres, 25° C., 20 hr.) and terminated when uptake of 2 moles of hydrogen is complete, the aminomethyl nitriles can be isolated in good yield, whereas the more severe conditions afford the bis-aminomethyl compounds in good yield.

Where the nitrile compound also carries a carboxamide or carboxylic ester group, the nitrile can be reduced to aminomethyl by either of the above procedures, without affecting the amide or ester group.

X (50)

Oxidation of III (33) is accomplished by treatment with diphenylseleninic anhydride in an inert solvent such as methylene chloride, 1,2-dichloroethane, or chloroform, at 0°–50° C. for 8–48 hr. to afford nitrile III (34).

Y (52)

Hydrolysis and reduction of III (6) is achieved by heating a dilute aqueous slurry at 50°–100° C. for 1–10 hr. until solution is complete. The water is evaporated and the dried residue is reduced with 3–4 eq. of diborane in in tetrahydrofuran at 25°–50° C. for 2–5 hr. followed by a mild (pH 1–3) aqueous acidic workup to afford III (35).

Z (55)

Treatment of III (37) with hydroxylamine (2–6 eq) in aqueous alcohol (methanol, ethanol) buffered to pH 6–7 at 10°–100° C. for 2–6 hr. affords the corresponding oxime. Dehydration can be effected by treatment with dehydrating agents such as acetic anhydride and heat, phosphorus trichloride, phosphorus pentachloride, phosphorus oxychloride, thionyl chloride, or chlorotrimethylsilane in inert solvents such as toluene, methylene chloride, chloroform, 1,2-dichloroethane, chlorobenzene or neat at temperatures of 20°–150° C. for 2–24 hr. to afford nitrile III (34).

AA (56)

Treatment of tricycle II (1) in a basic solvent such as pyridine or picoline in the presence of a tertiary base such as triethylamine, trimethylamine, ethyl(diisopropyl)amine, with hydrogen sulfide (g) at 10°–30° C. for 1–4 hr. affords the corresponding mono-thioamide II (5), which can be cyclized via a thermal workup to afford III (38).

AB (58, 58a, 58b)

Treatment of III (1), III (38), or II (1) with excess hydrogen sulfide in an alcoholic solvent (methanol, ethanol, isopropanol) with anhydrous ammonia at 60°–120° C. for 5–15 hr. affords III (39).

AE (68, 69, 76, 81)

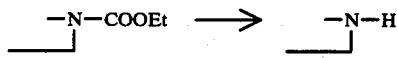

The urethane in concentrated hydrochloric acid is heated at 100°–140° C. for 2–24 hr. to afford the corresponding amine.

AF (71, 77, 82)

General Oxidation of an Amine to Aldehyde

The amine in 6–12N hydrochloric acid is heated at 40°–100° C. with 40% aqueous formaldehyde solution and an excess of hexamine in alcohols (methanol, ethanol, isopropanol) or acetic acid for 2–6 hr. to afford the corresponding aldehyde.

AG (73, 79, 84)

General Carbinol Oxidation

The carbinol is oxidized to the appropriate analgesic or analgesic precursor by treatment with an excess of manganese dioxide in an inert solvent such as benzene, acetonitrile, or cyclohexane at 25°–100° C. for 1–10 hr.

AH

Optical Resolution

The novel analgesics and intermediates may be resolved into their enantiomers by formation of diastereomeric salts with optically acids such as dibenzoyltartaric acid followed by fractional crystallization.

A further embodiment of this invention is the novel intermediate of structural formula:

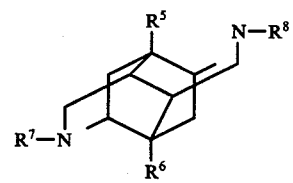

III or acid addition salt thereof, wherein R$^5$ and R$^6$ are the same or different and each is,

1. —CN

2. 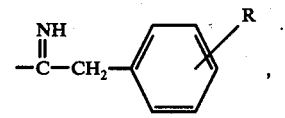

(2)

wherein R is lower alkoxy, especially $C_{1-3}$ alkoxy, fluoro, chloro, bromo, hydroxy, or hydrogen;
3. —COO(lower alkyl), especially —COO($C_{1-3}$ alkyl)
4. —CONH$_2$
5. —CO(halo), wherein halo is Cl, Br, or I
6. —COOH
7. —CH$_2$OH
8. —CHO
9. CH$_2$(halo) wherein halo is Cl, Br or I

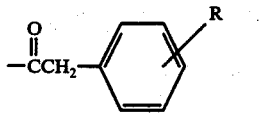 (10)

—CH$_2$NH$_2$ (11)

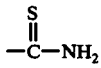 (12)

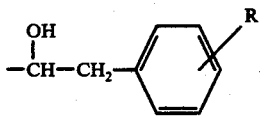 (13)

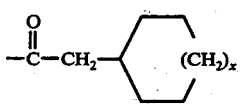 (14)

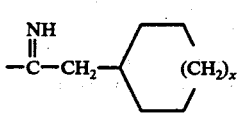 (15)

$R^7$ and $R^8$ are the same or different and each is
1. lower alkyl, especially $C_{1-6}$ alkyl,
2. lower alkenyl, especially $C_{2-6}$ alkenyl,
3. phenyl lower alkyl, especially benzyl, wherein the phenyl group can be unsubstituted or substituted with $C_{1-3}$ alkyl, $C_{1-3}$ alkoxy, or halo such as fluoro, chloro, or bromo,
4. hydrogen,
5. —COOBz,

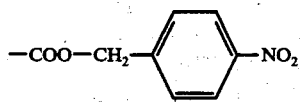 (6)

7. —COO(lower alkyl), especially —COO($C_{1-3}$ alkyl),
8. —COOCH$_2$CCl$_3$

A preferred embodiment of the novel intermediates of formula III or acid addition salt thereof is comprised of those compounds wherein: $R^5$ and $R^6$ are the same or different and each is
1. CN,

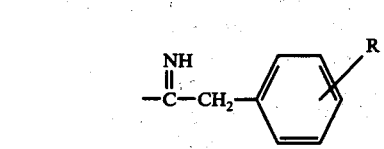 (2)

3. COO($C_{1-3}$ alkyl),
4. CONH$_2$,
5. CSNH$_2$, or

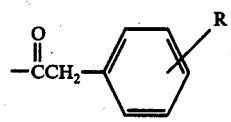 (6)

and $R^7$ and $R^8$ are the same or different and each is
1. lower alkyl, especially $C_{1-6}$ alkyl, or
2. hydrogen.

Another preferred embodiment of the novel intermediates of formula III is comprised of the enantiomers thereof having the same absolute configuration as the levorotatory enantiomer of 5,11-dimethyl-2,9-bis-phenylacetyldiazaditwistane.

A still further embodiment of this invention is the novel intermediate of structural formula:

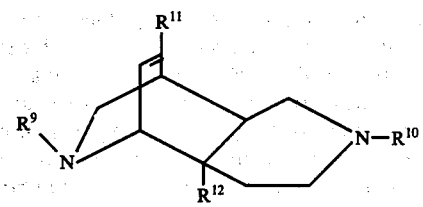

or acid addition salt thereof, wherein
$R^{11}$ and $R^{12}$ are the same or different and each is:
1. —CN,
2. —COO(lower alkyl), especially —COO($C_{1-3}$-alkyl),
3. —CONH$_2$,

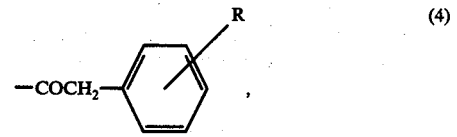 (4)

wherein R is lower alkoxy, especially $C_{1-3}$ alkoxy, fluoro, chloro, bromo, or hydrogen; and
$R^9$ and $R^{10}$ are the same or different and each is:
1. lower alkyl, especially $C_{1-6}$ alkyl,
2. lower alkenyl, especially $C_{2-6}$ alkenyl,
3. phenyl-lower alkyl, especially benzyl wherein the phenyl group can be unsubstituted or substituted with $C_{1-3}$ alkyl, $C_{1-3}$ alkoxy or halo such as fluoro, chloro, or bromo;
with the proviso that if $R^{11}$ and $R^{12}$ are -CN, then $R^9$ and $R^{10}$ are other than lower alkyl.

The acid addition salts of the novel intermediates include those prepared from organic, inorganic, organometallic, and Lewis acids.

As mentioned previously, the novel compounds of this invention with structural formula I are analgesic agents. As determined by the Haffner clamp test these compounds, as racemates, are up to three times as active as morphine, whereas the enantiomers with the same absolute configuration as the levorotatory enantiomer of 5,11-dimethyl-2,9-bis-phenylacetyldiazaditwistane are up to five times as active as morphine. Despite their unusual structure these novel compounds display the usual narcotic properties of a morphine analog including reversal of their analgesia by naloxone.

Another embodiment of this invention, therefore, is a novel method of treating pain in a warm blooded animal (including man) by the administration of a compound of formula I at the rate of 0.5 to 50 mg./kg./day, preferably from 4–15 mg./kg./day in a suitable pharmaceutical formulation, which is another embodiment of this invention, adapted for oral, topical parenteral, inhalation or rectal administration.

The pharmaceutical formulations for oral use may be in the form of tablets, troches, lozenges, aqueous or oral suspensions, dispersible powders or granules, emulsions, hard or soft capsules, syrups or elixirs and may be prepared according to methods known in the art for the manufacture of such compositions.

The pharmaceutical formulations for rectal use are in the form of suppositories prepared according to art recognized methods.

For topical use, creams, ointments, gels, solutions or suspensions are employed.

The pharmaceutical formulations for administration by injection are in the form of a sterile solution or suspension in a parenterally acceptable diluent or solvent.

The amount of active ingredient combined with the carrier materials of the pharmaceutical formulations to produce a single dosage form will vary depending on the mode of administration. For example, oral preparations should comprise from 5–500 mg., and preferably about 50–250 mg. of active compound in combination with the carrier materials.

The following are detailed experimental procedures for the preparation of the intermediates and final products of this invention. For the sake of clarity, the Examples are presented in groups corresponding to the grouping adopted for the general procedure descriptions, and each example is identified by the reaction number assigned in the flow charts. For instance, Example A1 is an example of the general procedure of Group A and specifically describes the process shown in reaction 1 of the flow sheets.

EXAMPLE A1

III(1): 2,9-Dicyano-5,11-dimethyldiazaditwistane

A slurry of 242.3 g. (1 mole) of endo-7,11-dicyano-4,9-dimethyl-4,9diazatricyclo[6.2.2.0$^{2,7}$]dodeca-11-ene [II(1)] in 2400 ml. of water was refluxed for 3 hours. After cooling in an ice-bath for 0.5 hr. the crystals were collected, washed with 3 × 400 ml. of water and dried in vacuo to yield 134.3 g. (55.4%) of 2,9-dicyano-5,11-dimethyldiazaditwistane, m.p. 204°–211° C.

Employing the above procedure in a variety of solvents produced the following results:

| Solvent | Temp. (° C.) | Time (Hrs.) | Yield (%) |
|---|---|---|---|
| methanol | 150 | 6 | 77.6 |
| isopropanol | 150 | 12 | 54 |
| t-butanol | 150 | 6 | slight |
| 2-methoxyethanol | 120–125 | 5 | 5 (estimate) |
| ethylene glycol | 125 | 4.5 | 38 |
| ethylene glycol | 150 | 6 | 66 |

EXAMPLE A9

III(5):
5,11-Dimethyl-2-methoxycarbonyl-9-carbamyldiazaditwistane

In a pressure vessel, 3.60 g. (17.2 mmol) of endo-7-carbamyl-11-methoxycarbonyl-4,9-dimethyl-4,9-diazatricyclo[6.2.2.0$^{2,7}$]dodeca-11-ene [II(2)] and 36 ml. of methanol were heated to 100° C. for 6 hours. The solvent was evaporated in vacuo to give 3.45 g. (95.8%) of 5,11-dimethyl-2-methoxycarbonyl-9-carbamyldiazaditwistane, m.p. 178°–182° C.

Employing reaction conditions substantially as described in Examples A1or A9, there are produced from the appropriately substituted 4,9 -diazatricyclo[6.2.2.0$^{2,7}$]-dodeca-11-enes (Compounds II), the following compounds:

III(15): 5,11-dibenzyl-2,9-dicyanodiazaditwistane;
III(20): 5,11-dibenzyl-2-methoxycarbonyl-9-carbamyldiazaditwistane;
III(38): 2-cyano-5,11-dimethyl-9-thiocarbamyldiazaditwistane;
I(2): 5,11-dimethyl-2,9-bis-phenylacetyldizaditwistane;
I(1): 5,11-dimethyl-2,9-bis-(3-methoxyphenylacetyl)-diazaditwistane;
III(40): 2,9-diacetyl-5,11-dimethyldiazaditwistane;

EXAMPLE B2

III(2):
5,11-Dimethyl-2,9-bis-phenylacetiminodiazaditwistane

A slurry of 7.26 g. (30 mmol) of 2,9-dicyano-5,11-dimethyldiazaditwistane in 75 ml. of tetrahydrofuran was treated under nitrogen with 45 ml. 2.0 molar benzylmagnesium bromide solution in tetrahydrofuran. After refluxing for 2 hours, the reaction mixture was cooled and quenched with 15 ml. of methanol at 20°–45° C. and with 150 ml. of water at 10°–20° C. The oil layer that formed was separated from the water layer, dissolved in 50 ml. of ether, dried over MgSO$_4$, and concentrated under vacuum to an oil. Addition of 56 ml. of methanol resulted in a crystal slurry which was filtered, washed with methanol and dried under vacuum to yield 9.27 g. (72.6%) of 5,11-dimethyl-2,9-bis-phenylacetiminodiazaditwistane, m.p. 155°–167° C.

EXAMPLE B3

I(1): 5,11-Dimethyl-2,9-bis-phenylacetyldiazaditwistane

A mixture of 6.75 g. (13.6 mmol) of Grignard product from Example B2 and 20 ml. of 2.5 N HCl and 10 ml. of water was washed with 50 × 25 ml. of benzene, aged for a total of 1 hour and basified with 25 ml. of 2.5 N sodium hydroxide. The product was extracted into 50 × 25 ml. of ethyl ether, dried over MgSO$_4$, and the solvent was evaporated to an oil. This was dissolved in 55 ml. of isopropanol panol and treated with 2.5 ml. of conc. hydrochloric acid. After stirring in an ice-bath for 15 min. the slurry was filtered, washed with ether, and dried to yield 6.33 gm. of 5,11-dimethyl-2,9-bis-phenylacetyldiazaditwistane hydrochloride, m.p. >250° C. (decomp.).

Calc. for C$_{28}$H$_{32}$N$_2$O$_2$.2HCl.0.5 H$_2$O;

Calc.: C, 65.87; H, 6.91; N, 5.48; Cl, 13.88; Found: C, 66.19 H, 6.81; N, 5.51; Cl, 13.71. Employing the procedure substantially as described in Examples B2 and B3, but substituting for racemic 2,9-dicyano-5,11-dimethyldiazaditwistane used in Example B2 an equimolecular amount of (−)- or (+)-2,9-dicyano-5,11-dimethyldiazaditwistane (from Example AH), there is produced (−)-5,11-dimethyl-2,9-bis-phenylacetyldiazaditwistane, m.p. 133°–135° C., [α]$_{578}$ −126.6° (c 0.55, CH$_2$Cl$_2$) and (+)-5,11-dimethyl-2,9-bis-phenylacetyldiazaditwistane, m.p. 118°–126° C., [α]$_{578}$ +127° (c 0.5, CH$_2$Cl$_2$).

Employing the procedure substantially as described in Examples B2 and B3 but substituting for the 90 mmol of benzylmagnesium bromide used in Example 2B, 13.5 mmole of cyclohexylmethylmagnesium bromide or cyclopentylmethylmagnesium bromide, followed by chromatography on silica gel using gradient elution from C₆H₆:CH₂Cl₂/1:1 to CH₂Cl₂:CH₃OH/99:1, there is produced 2-cyano-9-cyclohexylacetyl-5,11-dimethyldiazaditwistane, m.p. 89°–93° C. and 2-cyano-9-cyclopentylacetyl-5,11-dimethyldiazaditwistane, respectively.

Further treatment of the 2-cyano-9-cyclohexylacetyl-5,11-dimethyldiazaditwistane or 2-cyano-9-cyclopentylacetyl-5,11-dimethyldiazaditwistane with an excess of benzylmagnesium bromide by the method described in Examples B2 and B3, there is produced oily 2-cyclohexylacetyl-9-phenylacetyl-5,11-dimethyldiazaditwistane, picrate m.p. 185°–189° C., dipicrate, m.p. 215°–219° C., and 2-cyclopentylacetyl-9-phenylacetyl-5,11-dimethyldiazaditwistane, respectively.

EXAMPLE B10

I(1): 5,11-Dimethyl-2,9-bis-phenylacetyldiazaditwistane

A mixture of 2.93 g. (10 mmol) of 2-carbamyl-9-methoxycarbonyl-5,11-dimethyldiazaditwistane [III(5)], 29 ml. of tetrahydrofuran, and 20 ml. of 2.0 molar benzylmagnesium chloride were aged at room temperature overnight and acidified. By tlc estimate a yield of about 25% of 5,11-dimethyl-2,9-bis-phenylacetyldiazaditwistane was obtained. By substituting an equimolecular amount of 4-fluorobenzylmagnesium chloride or 4-methoxybenzylmagnesium chloride for the benzylmagnesium chloride used in Example B10, there are produced 5,11-dimethyl-2,9-bis-(4-fluorophenyl)acetyldiazaditwistane and 5,11-dimethyl-2,9-bis(3-methoxyphenyl)acetyldiazaditwistane, respectively.

EXAMPLE B49

III(33): 2-Aminomethyl-5,11-dimethyl-9-phenylacetyldiazaditwistane

A solution of 49.2 g. (b 200 mmol) of 2-aminomethyl-9-cyano-5,11-dimethyldiazaditwistane [III(32)] in 200 ml. of tetrahydrofuran was cooled in an ice-methanol mixture to −5° C. and treated with 400 ml. of 2.0 molar benzylmagnesium chloride solution in tetrahydrofuran over a period of 0.5 hr. The reaction mixture was stirred in an ice bath for 3 hr. and quenched at 5°–10° C. with 200 ml. of methanol, 48 ml. of 50% sodium hydroxide followed by 200 ml. of methanol. The precipitate of inorganic material was filtered and washed with 1.5 liters of methanol:methyene chloride mixture 1:1 (v/v). The solvent was evaporated, the residue dissolved in 400 ml. of 2.5 N HCl and neutral contaminants were removed by extraction into 4 × 100 ml. of methylene chloride. Basification of the hydrochloric acid solution with 70 ml. of 50% (w/v) sodium hydroxide solution, extraction into 3 × 50 ml. of methylene chloride and evaporation to dryness gave 52.7 g. (77.7%) as an oil whose IR, NMR, and mass spectra are in accord with the structure.

EXAMPLE B90

III(33): 2-Aminomethyl-5,11-dimethyl-9-phenylacetyldiazaditwistane

A reaction mixture of 1.00 g. (3.78 mmol) of 2-aminomethyl-9-carbamyl-5,11-dimethyldiazaditwistane [III(4a)], 5ml. tetrahydrofuran and 12 ml. of 2 molar benzylmagnesium chloride was refluxed for 1.5 hr. and then cooled and quenched with 5 ml. of methanol and 1 ml. of 50% (w/v) NaOH solution, concentrated in vacuo to a crystal mass which was extracted with 4 × 20 ml. of methylene chloride. The solvent was evaporated and the residue dissolved in 4 ml. of 2.5 N HCl, washed with hexane, basified with 6 ml. of 2.5 N NaOH solution, and the product was extracted into methylene chloride. The amorphous base obtained after concentration was dissolved in ether and converted to a trihydrochloride salt by HCl gas introduction. After filtering and drying 1.30 g. (76.6%) of 2-aminomethyl-5,11-dimethyl-9-phenylacetyldiazaditwistane was obtained. NMR and tlc were in accord with the structure. The mass spectrum of the free base shows the appropriate molecular ion at m/e 309.

EXAMPLE B91

III(33): 2-Aminomethyl-5,11-dimethyl-9-phenylacetyldiazaditwistane

A mixture of 5.60 g. (20 mmol) of 2-aminomethyl-9-methoxycarbonyl-5,11-dimethyldiazaditwistane [III(6a)] in 25 ml. of tetrahydrofuran with 30 ml. of 2.0 molar benzylmagnesium chloride was refluxed for 2 hr. The reaction mixture was quenched with 2.5 ml. 50% (w/v) NaOH solution, concentrated in vacuo and flushed with 3 × 100 ml. of methanol. The solid residue was extracted with 100 + 50 ml. of methanol, the extract was concentrated and the residue was dissolved in 20 ml. of 2.5 NHCl and washed with 2 × 20 ml. of hexane. Basification with 24 ml. 2.5 N NaOH followed by extraction with methylene chloride, drying, concentration to an amorphous mass, ether extraction, treatment of the extract with gaseous HCl, filtration and drying yields 2.40 g. (26.7%) of 2-aminomethyl-5,11-dimethyl-9-phenylacetyldiazaditwistane trihydrochloride. The NMR and tlc were in accord with the structure.

Following the procedures substantially as described in Examples B2, B10, B49, B90, or B91 (and B3 if applicable) on appropriately substituted diazaditwistane intermediates, there are produced the following compounds:

I(2): 5,11-diethyl-2,9-bis-phenylacetyldiazaditwistane
III(18): 2,9-bis-phenylacetiminodiazaditwistane
III(19): 2,9-bis-phenylacetyldiazaditwistane
I(4): 5-methyl-2,9-bis-phenylacetyldiazaditwistane
III(36): 2-hydroxymethyl-5,11-dimethyl-9-phenylacetyldiazaditwistane
III(45): 5,11-dimethyl-2,9-bis-(1-hydroxy-2-phenylethyl)-diazaditwistane
III(49): 5-methyl-2,9-bis-(1-hydroxy-2-phenylethyl)-diazaditwistane
III(53): 2,9-bis-(1-hydroxy-2-phenylethyl)diazaditwistane.

EXAMPLE C4

I(6): 2,9-Bis-(3-hydroxyphenylacetyl)-5,11-dimethyldiazaditwistane

A solution of 100 mmole of 2,9-bis-(3-methoxyphenylacetyl)-5,11-dimethyldiazaditwistane [I(1)] and 250 mmole of sodium thioethoxide in 500 ml. of dry dimethyl formamide under N₂ is refluxed for 3 hr. After addition of 250 mmole of gaseous HCl and concentration to dryness, the residue is recrystallized from ethyl acetate to afford pure 2,9-bis-(3-hydroxyphenylacetyl)-5,11-dimethyldiazaditwistane.

EXAMPLE E6

III(4):
2-Carbamyl-9-cyano-5,11-dimethyldiazaditwistane

The aqueous mother liquors from A1 were concentrated to a wet crystal mass which was extracted with 150 ml. of methanol and the extract was evaporated to a crystal mass which was dried, slurried with hot dry methanol, let cool to room temperature and filtered to give 14.3 g. (5.5%) of 2-carbamyl-9-cyano-5,11-dimethyldiazaditwistane, m.p. 229°–237° C. The NMR and IR spectra were in accord with the structure.

Anal. for $C_{14}H_{20}N_4O$. Calc.: C, 64.59; H, 7.74; N, 21.52; Found: C, 64.82; H, 7.77; N, 21.34.

EXAMPLE F8

II(2):
Endo-7-carbamyl-11-methoxycarbonyl-4,9-dimethyl-4,9-diazatricyclo[6.2.2.0$^{2,7}$]dodeca-11-ene A solution of 2.00 g. (20.6mmol) of II(1) in 15 ml. conc. sulfuric acid was heated at 100°. for 1 hour and added to 200 ml. of cooled methanol. The methanol was removed in vacuo and the residue was treated with 200 mmol. of sodium hydroxide in 75 ml. of water and extracted with 75 + 2 × 40 ml. $CH_2Cl_2$. The $CH_2Cl_2$ was dried and concentrated to yield 4.17 g. (68.9%) of ester-amide II(2), m.p. 162°–165° C., NMR and IR spectra were in accord with the structure.

Anal. for $C_{15}H_{23}N_3O_3$; Calc.: C, 61.41; H, 7.90; N, 14.32; Found: C, 61.02; H, 8.07; N, 14.00.

EXAMPLE F24

III(1a):
2,9-bis-Ethoxycarbonyl-5,11-dimethyldiazaditwistane

A solution of 9.7 g. of III(1) in 15 ml. of conc. $H_2SO_4$ was heated at 65° for 2.5 hr., cooled, treated with 100 ml. of ethanol and refluxed for 48 hr. After cooling the precipitate was filtered, triturated with $CH_2Cl_2$ and filtered. The $CH_2Cl_2$ solution was concentrated, slurried with 35 g. of $NaHCO_3$ in ethanol, filtered, concentrated and partitioned between 50 ml. of satd. $NaHCO_3$ and $CH_2Cl_2$. Concentration of the $CH_2Cl_2$ solution afforded 9.3 g. (69%) of 2,9-bis-ethoxycarbonyl-5,11-dimethyldiazaditwistane, m.p. 61°–66° C.

Anal. for $C_{18}H_{28}N_2O_4$: Calcd: C, 64.26; H, 8.38; N, 8.32; Found: C, 64.98; H, 8.22; N, 8.18.

EXAMPLE G11

III(6):
2-Cyano-5,11-dimethyl-9-methoxycarbonyldiazaditwistane

A slurry of 2.50 g. (8.5 mmol) of 2-carbamyl-5,11-dimethyl-9-methoxycarbonyldiazaditwistane [III(5)] in 10 ml. of dried pyridine was treated over a 10 min. period with 10 ml. of phosphorus oxychloride and heated in an oil bath at 105° C. for 2hr. After the bulk of the pyridine was removed in vacuo, the residue was cooled in dry ice-acetone and quenched with 50 ml. of methanol. The methanol was removed in vacuo and the residue was distributed between 100 ml. of 1N sodium hyroxide and methylene chloride. The organic phase was separated, dried and concentrated in vacuo to yield 1.30 g. (55%) of 2-cyano-5,11-dimethyl-9-methoxycarbonyldiazaditwistane, m.p. 109°–114° C. IR and NMR spectra were in accord with the assigned structure.

Anal. for $C_{15}H_{21}N_3O_2$ Calc.: C, 65.43; H, 7.69; N, 15.26; Found: C, 65.10; H, 7.80; N, 14.99.

EXAMPLE H13

III(7): 2,9-Dicarboxy-5,11-dimethyldiazaditwistane

A slurry of 20 g. (83 mmole) of endo-7,11-dicyano-4,9-dimethyl-4,9-diazatricyclo[6.2.2.0$^{2,7}$]dodeca-11-ene [II(1)] in 100 ml. of water was heated at 200° for 6 hr. in a pressure bomb. The resulting dark solution was treated with 1.0 g. of Darco G-60, filtered and concentrated at 60°/vac. to a brown gum. This was triturated with 100 ml. of isopropanol, and the resulting solid was filtered, washed with 2 × 25 ml. of isopropanol and dried at 100°/1mm overnight to afford 20.5 g. (73 mmole, 88%) of 2,9-dicarboxy-5,11-dimethyldiazaditwistane, m.p.>300°. The NMR spectrum was in accord with the structure.

Anal. for $C_{14}H_{20}N_2O_4 \cdot 0.5H_2O$ Calc.: C, 58.1; H, 7.5; N, 9.6; Found: C, 58.1; H, 7.3; N, 9.7.

EXAMPLE I14

III(8):
2,9-bis-Chlorocarbonyl-5,11-dimethyldiazaditwistane

A mixture of 80 g. (26.8 mmol) 2,9-dicarboxy-5,11-dimethyldiazaditwistane [III(7)] and 400 ml. of thionyl chloride was refluxed for 18 hr., cooled to room temperature and then were filtered, washed with 3 ×100 ml. of methylene chloride and dried at 60° C. overnight to yield 139.6 g. of crude 2,9-bis-chlorocarbonyl-5,11-dimethyldiazaditwistane hydrochloride which was used without further purification.

EXAMPLE J16

III(9): 2,9-Dicarbamyl-5,11-dimethyldiazaditwistane

A mixture of 2.0 g. (17.0 mmole) of 2-carbamyl-5,11-dimethyl-9-methoxycarbonyldiazaditwistane [III(5)], 20 ml. of methanol and 20 ml. of liquid ammonia was heated at 50° for 2 hr. in a closed vessel. The reaction mixture was concentrated, triturated with 50 ml. of $H_2O$ and filtered to give 4.5 g. of 2,9-dicarbamyl-5,11-dimethyldiazaditwistane, m.p.>290°.

Anal. for $C_{14}H_{22}N_4O_2$. Calcd.: C, 60.40; H, 7.97; N, 20.13; Found: C, 60.10; H, 7.88; N, 19.97.

Employing the procedure substantially as described in Example J16, but starting with 2,9-bis-chlorocarbonyl-5,11-dimethyldiazaditwistane [III(8)] or 5,11-dibenzyl-2,9-dimethoxycarbonyldiazaditwistane [III(23)], there is produced 2,9-dicarbamyl-5,11-dimethyldiazaditwistane [III(9)], or 2,9-dicarbamyl-5,11-dibenzyldiazaditwistane [III(22)], respectively.

EXAMPLE K18

III(10):
2,9-bis-hydroxymethyl-5,11-dimethyldiazaditwistane

One liter of 1 molar borane-tetrahydrofuran complex was added rapidly to a well agitated slurry of 40.0 g. (143 mmol) of 2,9-dicarboxy-5,11-dimethyldiazaditwistane [III(7)]. With good stirring to allow for gas evolution, the mixture was heated to reflux and held for 4 hr. After cooling to 10° C., 100 ml. of methanol was added over a 1.5 hr. period and the solution was evaporated in vacuo to an amorphous mass which was flushed with 3 × 200 ml. of methanol. The residue was dissolved in 80 ml. of water, cooled in an ice-bath, digested by very slow addition of 80 ml. of conc. HCl and then refluxed for 2 hr. The small amount of solids forming on cooling were filtered and discarded. The filtrate was basified with 160 ml. of 25% sodium hydroxide and extracted with 4 × 300 ml. of methylene chloride. After removal of the solvent, the remaining crystals were slurried and washed with a total of 200 ml. of ether and dried to give 18.2 g. (50.5%) of 2,9-bis-hydroxymethyl-5,11-dimethyldiazaditwistane, m.p. 120°–128° C., NMR and IR spectra were in accord with the structure.

EXAMPLE L19

III(11): 2,9-bis-Chloromethyl-5,11-dimethyldiazaditwistane

A slurry of 4.00 g. (15.8) of the dialcohol [III(10)] from Example K18 in 40 ml. of thionylchloride was refluxed for 20 hr., concentrated in vacuo to a crystal mass and treated with 40 ml. of ice. After basification with 45 ml. 2.5 N sodium hydroxide, extraction with methylene chloride, drying and evaporation, there was obtained 3.02 g. (66%) of 2,9-bis-chloromethyl-5,11-dimethyldiazaditwistane, m.p. 70°–84° C. Recrystallization from 60 ml. of petroleum ether yielded 2.85 g; m.p. 79°–84° C., IR and NMR spectra were in accord with the structure.

Employing the procedure substantially as described in Example L19 on Compound III (36), 2-hydroxymethyl-5,11-dimethyl-9-phenylacetyldiazaditwistane, there is produced 2-chloromethyl-5,11-dimethyl-9-phenylacetyldiazaditwistane.

EXAMPLE M(20)

2,9-Diformyl-5,11-dimethyldiazaditwistane

A solution of 50 mmole of III(11) in 50 ml. of hexamethylphosphoramide is heated at 190° for 6 hr. After cooling the reaction is poured onto 500 g. of water. The resulting mixture is extracted with 5 × 100 ml. of $CHCl_3$, which is backwashed with 2 × 100 ml. of $H_2O$, dried over $MgSO_4$, filtered and concentrated to afford the crude dialdehyde [III(14)] which is recrystallized to afford pure product.

EXAMPLE P23

III(14): 2,9-Diformyl-5,11-dimethyldiazaditwistane

A solution of 100 mmole of alcohol [III(10)], 2,9-bis-hydroxymethyl-5,11-dimethyldiazaditwistane, in 500 ml. of benzene is treated with 250 ml. of activated $MnO_2$ at reflux with continuous water removal. After 12 hr. the mixture is cooled, filtered, and concentrated to a volume of 150 ml. Hexane (100 ml.) is added and the resulting precipitate is filtered, washed and dried at 50° in vacuo to give 2,9-diformyl-5,11-dimethyldiazaditwistane.

EXAMPLE R86, 87

II(3): endo-7,11-Dicyano-4,9-dibenzyl-4,9-diazatricyclo[6.2.2.0$^{2,7}$]dodeca-11-ene To a solution of 10 mmole of $NaBH_4$ and 10 mmole of NaOH in 50 ml. of $CH_3OH$ at −20° is added portionwise over 30 min. 10 mmole of N-benzyl-4-cyanopyridinium chloride. The resulting slurry is stirred for 1 hr., warmed to 25° and filtered to afford the corresponding Diels-Alder adduct of the dihydropyridine.

To a solution of the adduct (10 mmole) in 50% aqueous methanol buffered to pH 4 is added 5 mmole of $NaBH_3CN$ over 10 min. and the resulting mixture is stirred for 1 hr. Quenching onto ice, extraction with $CH_2Cl_2$ and evaporation affords the tricyclic adducts II(3), endo-7,11-dicyano-4,9-dibenzyl-4,9-diazatricyclo[6.2.2.0$^{2,7}$]dodeca-11-ene.

Employing the procedure substantially as described in Example R86,87, but substituting for the starting material used therein an equimolecular amount of N-benzyl-4-phenylacetylpyridinium chloride, N-(n-butyl)-4-cyanopyridinium chloride, or N-(n-hexyl)-4-phenylacetylpyridinium chloride, there is produced respectively: endo-7,11-bis-phenylacetyl-4,9-dibenzyl-4,9-diazatricyclo[6.2.2.0$^{2,7}$]dodeca-11-ene, endo-7,11-dicyano-4,9-di(n-butyl)-4,9-diazatricyclo[6.2.2.0$^{2,7}$]dodeca-11-ene; or endo-7,11-bis-phenylacetyl-4,9-di(n-hexyl)-4,9-diazatricyclo[6.2.2.0$^{2,7}$]dodeca-11-ene.

EXAMPLE S26

III(16): 2,9-Dicyanodiazaditwistane

A solution of 10 mmole of 5,11-dibenzyl-2,9-dicyanodiazaditwistane, compound [III(15)], in 50 ml. of ethanol is hydrogenated over 0.1 g. of $PtO_2$ at 40 psi $H_2$ and 25° for 1 hr. After filtration, addition of 100 ml. of water to the filtrate affords 2,9-dicyanodiazaditwistane, which is isolated by filtration.

Employing the procedure substantially as described in Example S26, but substituting for the starting material used therein an equimolecular amount of:

III(20): 2-carbamyl-5,11-dibenzyl-9-methoxycarbonyldiazaditwistane;
III(21): 2-cyano-5,11-dibenzyl-9-methoxycarbonyldiazaditwistane;
III(22): 5,11-dibenzyl-2,9-dicarbamyldiazaditwistane; or
III(23): 5,11-dibenzyl-2,9-dimethoxycarbonyldiazaditwistane; respectively, there is produced:

III(24): 2-carbamyl-9-methoxycarbonyldiazaditwistane;
III(25): 2-cyano-9-methoxycarbonyldiazaditwistane;
III(26): 2,9-dicarbamyldiazaditwistane; or
III(27): 2,9-dimethoxycarbonyldiazaditwistane.

Similarly, but employing palladium on carbon as catalyst:

III(28): 5,11-bis-benzyloxycarbonyl-2,9-dicyanodiazaditwistane;
III(29): 2,9-dicyano-5-benzyloxycarbonyl-11-methyldiazaditwistane;
2,9-dicyano-5,11-bis-p-nitrobenzyloxycarbonyldiazaditwistane;

provide respectively

III(16): 2,9-dicyanodiazaditwistane;
III(30): 2,9-dicyano-5-methyldiazaditwistane; and
III(16): 2,9-dicyanodiazaditwistane.

EXAMPLE T42

I(2): 5,11-Diethyl-2,9-bis-phenylacetyldiazaditwistane

A mixture of 2,9-bis-phenylacetyldiazaditwistane [III(19)] (2.01 g., 5.0 mmol), EtI (1.72 g., 11 mmol), $K_2CO_3$ (1.5 g., 11 mmol) and DMF (25 ml.) was stirred at ambient temperature for 70 hr. Addition of water (100 ml.) was followed by extraction with 2 × 60 ml. of $CH_2Cl_2$. This was washed with $H_2O$ (3 × 25 ml.), dried ($MgSO_4$) and concentrated to an oil (1.9 g.). Generation of the HCl salt ($CH_2Cl_2$, $Et_2O$, HCl), followed by washing ($CH_2Cl_2$, $Et_2O$), dissolution in 2.5N aqueous HCl, washing ($CH_2Cl_2$) and regeneration (2.5N NaOH), extraction ($CH_2Cl_2$) and evaporation afforded the free base as an amorphous mass. Regeneration of the HCl salt ($Et_2O$, HCl) afforded 0.93 g. of solvated dihydrochloride (single spot by tlc) which was recrystallized from 3 ml. EtOH. Regeneration (2.5N NaOH), extraction (CH$_2$Cl$_2$) and concentration afforded the crystalline free base of 5,11-dimethyl-2,9-bis-phenylacetyldiazaditwistane, m.p. 105°–112°.

Anal. for C$_{30}$H$_{36}$N$_2$O$_2$: Calcd: C, 78.91; H, 7.95; N, 6.13. Found: C, 78.49; H, 7.79; N, 5.98.

EXAMPLE T47

I(3):

5-Ethyl-11-methyl-2,9-bis-phenylacetyldiazaditwistane

A mixture of the free base of 11-methyl-2,9-bis-phenylacetyldiazaditwistane [I(4)] (2.50 g., 6.25 mmol), EtI (1.03 g., 6.6 mmol), K$_2$CO$_3$ (0.915 g., 6.6 mmol) and DMF (25 ml.) was stirred at ambient temperature overnight. The reaction mixture was partitioned between H$_2$O (100 ml.) and CH$_2$Cl$_2$ (100 ml.) and the residue obtained by drying and concentrating the CH$_2$Cl$_2$ solution was chromatographed on silica gel (100 g., Baker 3405) using EtOAc: CH$_3$OH:HOAc/50:4:1. The product containing fractions were concentrated, and the residue dissolved in CHCl$_3$ and filtered. The oil resulting from the subsequent introduction of HCl gas was recrystallized by addition of Et$_2$O, filtered and recrystallized from ethanol (6 ml.) to give 0.42 g. (12.5% of the hydrochloride of 5-ethyl-11-methyl-2,9-bis-phenylacetyldiazaditwistane.

Anal. for C$_{29}$H$_{34}$N$_2$O$_2$·2HCl.1.2H$_2$O): Calcd: C, 64.84; H, 7.20; Cl, 13.20; N, 5.21. Found: C, 64.69; H, 6.98; Cl, 13.51; N, 5.14.

Employing the procedure substantially as described in Example T42 and T47 but substituting for the starting materials used therein, an equimolar amount of:
III(16): 2,9-dicyanodiazaditwistane; or
III(19): 2,9-bis-phenylacetyldiazaditwistane;
there is produced respectively
III(17): 5,11-diethyl-2,9-dicyanodiazaditwistane, or
I(2): 5,11-diethyl-2,9-bis-phenylacetyldiazaditwistane.

EXAMPLE V74

III(46):

2,9-Dicyano-5-ethoxycarbonyl-11-methyldiazaditwistane and

III(50):

2,9-Dicyano-5,11-bis-ethoxycarbonyldiazaditwistane

A mixture of 36 g. (150 mmol) of 2,9-dicyano-5,11-dimethyldiazaditwistane [III(1)], 260 ml. of benzene and 360 ml. of ethylchloroformate was refluxed for 30 hr. A small amount of insoluble solids was removed by filtration and the filtrate was concentrated under vacuum to a solid mass which was washed with 100 ml. 1 N HCl, taken up in a mixture of 200 ml. of benzene, and 200 ml. of methylene chloride. After extracting the organic phase with 100 ml. 0.5 N HCl and a waterwash, it was dried and evaporated under vacuum to yield 28.0 g. (56%) of 2,9-dicyano-5,11-bis-ethoxycarbonyldiazaditwistane, m.p. 193°–195° C.

Anal. for C$_{18}$H$_{22}$N$_4$O$_4$ Calcd.: C, 60.32; H, 6.12; N, 15.63. Found: C, 60.54; H, 6.05; N, 15.54.

The acidic aqueous washes were concentrated under vacuum to a crystal mass of 2,9-dicyano-5-ethoxycarbonyl-11-methyldiazaditwistane, III(46), 17.32 g. (32.5%) m.p. 255°–270° C.

Anal. for C$_{16}$H$_{20}$N$_4$O$_2$·HCl Calcd.: C, 57.06; H, 6.48; N, 16.63; Cl, 10.53. Found: C, 56.87; H, 6.15; N, 16.45; Cl, 10.87.

Employing the procedure substantially as described in Example V74 but substituting for the starting material used therein an equimolecular amount of 5,11-dimethyl-2,9-bis-phenylacetyldiazaditwistane [I(1)], there is produced 5-ethoxycarbonyl-11-methyl-2,9-bis-phenylacetyldiazaditwistane [III(42)] and 5,11-bis-ethoxycarbonyl-2,9-bis-phenylacetyldiazaditwistane [III(43)].

Employing the procedure of Example V74 but substituting for the ethylchloroformate used therein, an equimolecular amount of benzylchloroformate, there is produced 5,11-bis-benzyloxycarbonyl-2,9-dicyanodiazaditwistane [III(28)] and 5-benzyloxycarbonyl-11-methyl-2,9-dicyanodiazaditwistane [III(29)].

Similarly, treatment of 5,11-di(n-butyl)-2,9-dicyanodiazaditwistane with p-nitrobenzylchloroformate produces 5,11-bis-p-nitrobenzyloxycarbonyl-2,9-dicyanodiazaditwistane and treatment of 5,11-di(n-hexyl)-2,9-bis-phenylacetyldiazaditwistane with trichloroethylchloroformate produces 5,11-bis-trichloroethoxycarbonyl-2,9-bis-phenylacetyldiazaditwistane.

EXAMPLE W48

III(32):

2-Aminomethyl-9-cyano-5,11-dimethyldiazaditwistane

A mixture of 24.20 g. (100 mmol) of 2,9-dicyano-5,11-dimethyldiazaditwistane [III(1)], 240 ml. of ethanol, 24 g. of liquid NH$_3$ and 1 teaspoon of Raney nickel was shaken under 40 psi of hydrogen until theoretical uptake was observed. The catalyst was removed by filtration and the filtrate concentrated in vacuo to an oil. This was dissolved in ether, about 6% of unreacted starting material was removed by filtration and the solvent was evaporated. The residue was distributed between 75 ml. of methylene chloride and 5 ml. of water. The water layer was extracted with 50 + 2 × 25 ml. of methylene chloride. Each extract was washed sequentially with the same 5 ml. of water, repeating the sequence 6 times. The methylene chloride extracts were combined and concentrated in vacuo to yield 18.17 g. (73.6%) of 2-aminomethyl-9-cyano-5,11-dimethyldiazaditwistane, m.p. 111°–115° C.

The aqueous washes were concentrated in vacuo to yield 4.25 g. (17.0%) of 2,9-bis-aminomethyl-5,11-dimethyldiazaditwistane [III(44)] by comparison with an authentic sample.

EXAMPLE W70

III(44):

2,9-bis-Aminomethyl-5,11-dimethyldiazaditwistane

In a pressure vessel 61.0 g. (251 mmol) of 2,9-dicyano-5,11-dimethyldiazaditwistane [III(1)], 500 ml. of ethanol, 100 ml. of liquid ammonia, and 1.5 teaspoon of Raney nickel were treated with 2200 psi of hydrogen at 80° C. for 48 hr. The system was cooled, vented, and the catalyst was removed by filtration. After solvent removal, the residual mass crystallized with 500 ml. of ether, filtered, and dried in vacuo to yield 57.2 g. (91%) of 2,9-bis-aminomethyl-5,11-dimethyldiazaditwistane m.p. 105°–111° C.

EXAMPLE W75

III(55):
2,9-bis-Aminomethyl-5-methyl-11-ethoxycarbonyl-diazaditwistane

A mixture of 5.00 g. (14.8 mmol) of 2,9-dicyano-5-methyl-11-ethoxycarbonyldiazaditwistane [III(46)], hydrochloride, 50 ml. of ethanol, 10 ml. of liquid ammonia, and 0.25 teaspoon of Raney nickel was treated in a pressure system with 2300 psi of hydrogen at 80° C. for 48 hr. The system was cooled, vented and the catalyst removed by filtration through super cell. The filtrate was concentrated under vacuum to a crystal mass. Treatment with gaseous HCl in either afforded after filtration the trihydrochloride dihydrate of 2,9-bis-aminomethyl-5-methyl-11-ethoxycarbonyldiazaditwistane in 5.22 gm. yield (77%).

Anal. for $C_{16}H_{29}N_4O_2 \cdot 3HCl \cdot 2H_2O$ Calc.: C, 42.25; H, 7.98; N, 12.31; Cl, 23.38; Found: C, 42.82; H, 7.76; N, 11.94; Cl, 23.68.

EXAMPLE W80

III(54):
2,9-bis-Aminomethyl-5,11-bis-ethoxycarbonyldiazaditwistane

A mixture of 5.0 g. (14.0 mmol) of 2,9-dicyano-5,11-bis-ethoxycarbonyldiazaditwistane [III(50)], 50 ml. of ethanol, 10 ml. of liquid $NH_3$ and 0.25 teaspoon of Raney nickel was treated in a pressure vessel with 1800 psi of hydrogen at 80° C. for 48 hr. The system was cooled, vented and the catalyst removed by filtration. The filtrate was concentrated in vacuo to an oil which was pumped overnight. On addition of 5 ml. of ether crystals formed which were collected and washed with ether to yield 3.51 g. (68.4%) of 2,9-bis-aminomethyl-5,11-bis-ethoxycarbonyldiazaditwistane, m.p. 105°–108° C.

Anal. for $C_{18}H_{30}N_4O_4$. Calc.: C, 59.00; H, 8.25; N, 15.29. Found: C, 59.02; H, 8.47; N, 15.12.

EXAMPLE W88

III(4a):
2-Aminomethyl-9-carbamyl-5,11-dimethyldiazaditwistane

A mixture of 11.30 g. (43.4 mmol) of -carbamyl-9-cyano-5,11-dimethyldiazaditwistane [III(4)], 100 ml. of ethanol, 44 g. of ammonia and 0.25 teaspoon of Raney nickel was treated at 80° C. with 2400 psi of hydrogen for 48 hr. The system was cooled, vented and the catalyst was removed by filtration through super cell. The filtrate was concentrated and the residue was triturated with ether to yield 9.77 g. (85.1%) of 2-aminomethyl-9-carbamyl-5,11-dimethyldiazaditwistane, m.p. 175°–182° C.

Anal. for $C_{14}H_{14}N_4O$: Calc.: C, 63.61; H, 9.15; N, 21.19; Found: C, 63.36; H, 9.51; N, 20.66.

EXAMPLE W89

III(6a):
2-Aminomethyl-9-methoxycarbonyl-5,11-dimethyldiazaditwistane

A mixture of 1.00 g. (3.6 mmol) of 2-cyano-9-methoxycarbonyl-5,11-dimethyldiazaditwistane [III(6)], 10 ml. of methanol and ⅛ tsp. of Raney nickel was heated to 80° C. under 2400 psi hydrogen for 48 hr. The system was cooled, the catalyst removed, and the solvent evaporated to yield an oil, whose spectral characteristics were in accord with the structure.

EXAMPLE X50

III(34):
2-Cyano-5,11-dimethyl-9-phenylacetyldiazaditwistane

A solution of 50 mmole of 2-aminomethyl-5,11-dimethyl-9-phenylacetyldiazaditwistane [III(33)] and 50 mmole of diphenylseleninic anhydride in 200 ml. of methylene chloride is stirred at 25° for 24 hours. The reaction mixture is partitioned between $CH_2Cl_2$ (250 ml.) and 1 N NaOH (250 ml.) and the $CH_2Cl_2$ layer is separated and dried over $Na_2SO_4$. After filtration and concentration, the residue is chromatographed on 500 g. of silica, thus affording a solution of 2-cyano-5,11-dimethyl-9-phenylacetyldiazaditwistane, which is isolated by concentration.

EXAMPLE Y52

III(35):
2-Cyano-9-hydroxymethyl-5,11-dimethyldiazaditwistane

2-Cyano-9-methoxycarbonyl-5,11-dimethyldiazaditwistane [III(6)], (50 mmole) is slurried in 500 ml. of $H_2O$ and warmed at 60° for 5 hr. until solution is complete. The water is removed at reduced pressure and the residue dried at 75°/vac. The resulting acid is reduced in a manner similar to that described in Example K18, thereby affording 2-cyano-9-hydroxymethyl-5,11-dimethyldiazaditwistane.

EXAMPLE Z55

III(34):
2-Cyano-5,11-dimethyl-9-phenylacetyldiazaditwistane

2-Chloromethyl-5,11-dimethyl-9-phenylacetyldiazaditwistane [III(37)] (100 mmole) and 250 ml. of hydroxylamine hydrochloride in 250 ml. of ethanol is adjusted to pH 6–7 with 10% NaOH and refluxed for 6 hr. The ethanol is removed at reduced pressure and the residue is maintained at pH 9–10 and 10° while acetic anhydride (500 mmole) is added over 1 hr. The mixture is extracted with 4 × 100 ml. of toluene which is combined, concentrated to 100 ml. at 1 atmosphere, refluxed for 3 hr. and taken to dryness to afford 2-cyano-5,11-dimethyl-9-phenylacetyldiazaditwistane.

EXAMPLE AA56

III(38):
2-Cyano-5,11-dimethyl-9-thiocarbamyldiazaditwistane

A slow stream of hydrogen sulfide was introduced for 6 hr. into a mixture of 19.40 g. (80 mmol) of endo-7,11-dicyano-4,9-dimethyl-4,9-diazatricyclo[6.2.2.0$^{2,7}$]-dodeca-11-ene [II(1)] and 9.7 mol of triethylamine in 96 ml. of pyridine to afford crude II(5). The mixture was concentrated at 60°–80° to a crystal mass, slurried with 50 ml. of methanol, filtered, washed with 3 × 15 ml. of methanol, and dried to yield 15.60 g. (70.5%) of 2-cyano-5,11-dimethyl-9-thiocarbamyldiazaditwistane, m.p. 225°–230° C.

Anal. for $C_{14}H_{21}N_4S$ Calc.: C, 60.83; H, 7.29; N, 20.70; S, 11.60; Found: C, 90.93; H, 7.42; N, 20.28; S, 11.82.

Compound III(38) can also be made from Compound III(1) under the same conditions in 49.4% yield, m.p. 229°–232° C.

EXAMPLE AB58

III(39): 5,11-Dimethyl-2,9-bis-thiocarbamyldiazaditwistane

A mixture of 4.84 g. (20 mmol) of 2,9-dicyano-5,11-dimethyldiazaditwistane [III(1)], 20 ml. of ethanol, 13 g. of liquid ammonia and 12.5 g. of hydrogen sulfide were heated at 80° C. for 8 hr. The system was vented and the reaction mixture was transferred with 10 ml. of methanol to a filter, washed with 3 × 6 ml. of methanol and dried to yield 5.89 g. (95%) of 5,11-dimethyl-2,9-dithiocarbamyldiazaditwistane, m.p. 226°–232° C.

Anal. for $C_{14}H_{22}N_4S$ Calc. C, 54.16; N, 7.14; N, 18.04; S, 20.65; Found: C, 54.13; H, 7.15; N, 17.84; S, 20.73.

It is also possible to make this compound directly from Compounds II(1) or III(38) by the same procedure.

EXAMPLE AE76

III(47): 2,9-bis-aminomethyl-5-methyldiazaditwistane

A mixture of 10.0 g. (32 mmol) of 2,9-bis-aminomethyl-5-methyl-11-ethoxycarbonyldiazaditwistane [III(55)], and 100 ml. of concentrated hydrochloric acid were heated in a pressure vessel at 120° C. for 12 hr. After cooling in an ice bath for 1 hr. the crystals were filtered, and dried at 78° C. for 17 hr. at 1 mm vacuum to yield 10.1 g. (87.41%) of 2,9-bis-aminoethyl-5-methyldiazaditwistane, NMR and IR are in accord with the structure.

Similarly, 5-ethoxycarbonyl-11-methyl-2,9-bis-phenylacetyldiazaditwistane and 5,11-bis-ethoxycarbonyl-2,9-bis-phenylacetyldiazaditwistane provide on hydrolysis 5-methyl-2,9-bis-phenylacetyldiazaditwistane and 2,9-bis-phenylacetyldiazaditwistane, respectively.

EXAMPLE AE81

III(51): 2,9-bis-aminomethyldiazaditwistane

A mixture of 60.0 g. (164 mmol) of 2,9-bis-aminomethyl-5,11-bis-ethoxycarbonyldiazaditwistane [III(54)], and 600 ml. of concentrated hydrochloric acid were heated in a pressure vessel at 120° C. for 8 hrs. After cooling in an ice bath for 2 hr. the crystals were filtered and washed with ice water. The product was dried at 78° C. for 20 hr. in 1 mm. vacuum to yield 60.4 g. (99.5%) of 2,9-bis-aminomethyldiazaditwistane.

Anal. for $C_{12}H_{22}N_4 \cdot 4HCl$ Calc.: C, 39.15; H, 7.12; Cl, 38.52; N, 15.22; Found: C, 39.09; H, 7.24; Cl, 38.19; N, 14.93.

EXAMPLE AF71

III(14): 2,9-Diformyl-5,11-dimethyldiazaditwistane

A solution of 100 mmole of amine 2,9-bis-aminomethyl-5,11-dimethyldiazaditwistane [III(44)], 48 ml. of concentrated HCl, 20 ml. of 40% aqueous HCOH, 33 g. of hexamine and 180 ml. of 50% aqueous acetic acid is heated at reflux for 3 hr. The solution is extracted with 100 ml. of benzene, adjusted to pH 12 with concentrated NaOH, and extracted with 5 × 100 ml. of $CH_2Cl_2$ which is dried over $Na_2SO_4$, filtered and concentrated. The residue is recrystallized from cyclohexane to afford 2,9-diformyl-5,11-dimethyldiazaditwistane.

EXAMPLE AG73

I(1): 5,11-Dimethyl-2,9-bis-phenylacetyldiazaditwistane

A solution of 100 mmole of 5,11-dimethyl-2,9-bis-(2-phenyl-1-hydroxyethyl)diazaditwistane [III(45)] in 500 ml. of acetonitrile is treated with 200 mmole of freshly prepared $MnO_2$ under reflux for 4 hr. with rapid stirring. The resulting mixture is filtered, concentrated and the residue recrystallized from benzene to afford 5,11-dimethyl-2,9-bis-phenylacetyldiazaditwistane.

EXAMPLE AH (−) and (+)-III(1): (−) and (+)-2,9-Dicyano-5,11-dimethyldiazaditwistane Resolution: A solution of 12.12 g. (50.0 mmole) of racemic 2,9-dicyano-5,11-dimethyldiazaditwistane [III(1)] in 500 ml. of refluxing methanol was treated with a hot solution of 18.7 g. (52.5 mmole) of dibenzoyl-D-tartaric acid (52.2 mmole) in 200 ml. of methanol. On cooling granular crystals formed first and after 1 hr. flocculent crystals started to separate. The mixture was warmed to dissolve the latter and filtered. The solid was washed with methanol and dried to yield 12.25 g. of granular crystals of the mono-salt of the (−)-isomer. On aging for 24 hr. the filtrate yielded a flocculent crystal mass which was filtered, washed with methanol and dried to yield 8.7 g. of the mono-salt of the (+)-isomer. The granular salt of the (−)-isomer was twice recrystallized from 40 volumes of methanol and converted to the free base by distribution between 60 ml. of satd. $NaHCO_3$ solution and 150 ml. of methylene chloride. After separation and evaporation of the methylene chloride there was obtained 3.40 g. (56%) of the (−)-isomer of 3: m.p. 249°–253°; $[\alpha]_{578}$ −220.8, $[\alpha]_{546}$ −250.6, $[\alpha]_{436}$ −426.0, $[\alpha]_{405}$ −509.0 $[\alpha]_{365}$ −660.2 (c 0.52, $CH_2Cl_2$). The flocculent salt of the (+)-isomer was twice recrystallized from 30 volumes of methanol and converted to the free base as above to yield 2.06 g. (36%) of the (+)-isomer of 3: m.p. 249°–253°; $[\alpha]_{258}$ +223.1, $[\alpha]_{546}$ +254.1, $[\alpha]_{436}$ +431.6, $[\alpha]_{405}$ +517.1, $[\alpha]_{365}$ +666.3 (c 0.53, $CH_2Cl_2$).

Following the procedure substantially as described in Example AH but substituting for the racemic starting material used therein, an equimolar amount of any of the novel racemic intermediates or starting materials such as 5,11-dimethyl-2,9-bis-phenylacetyldiazaditwistane, there are produced the corresponding enantiomers such as (−)- and (+)-5,11-dimethyl-2,9-bis-phenylacetyldiazaditwistane.

What is claimed is:

1. A process for the preparation of a compound of structural formula:

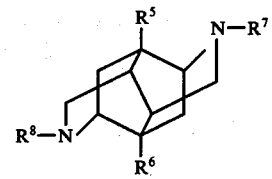

wherein
$R^5$ and $R^6$ are the same or different, and each is
1. CN,
2. COO(lower alkyl),
3. $CONH_2$,

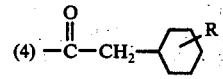

5. $CSNH_2$, $R^7$ and $R^8$ are 1. lower alkyl,
2. lower alkenyl, or
3. phenyl-lower alkyl, wherein the phenyl is unsubstituted or substituted with $C_{1-3}$ alkyl, $C_{1-3}$ alkoxy, or halo, which comprises heating a compound of structural formula:

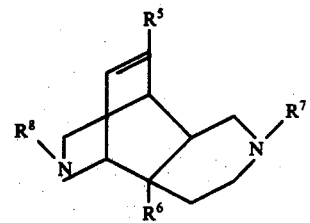

in water or a lower alkanol.

2. The process of claim 1, wherein $R^5$ and $R^6$ are —CN, COOCH$_3$, or CONH$_2$, and $R^7$ and $R^8$ are methyl.

3. The process of claim 1, wherein $R^5$ and $R^6$ are —CN and $R^7$ and $R^8$ are methyl.

* * * * *